United States Patent [19]
Kleber et al.

[11] Patent Number: 5,064,640
[45] Date of Patent: * Nov. 12, 1991

[54] ANTICARIOGENIC COMPOSITIONS

[75] Inventors: Carl J. Kleber; Mark S. Putt, both of Ft. Wayne, Ind.

[73] Assignee: Purdue Research Foundation, West Lafayette, Ind.

[ * ] Notice: The portion of the term of this patent subsequent to Dec. 11, 2007 has been disclaimed.

[21] Appl. No.: 592,060

[22] Filed: Oct. 3, 1990

Related U.S. Application Data

[60] Division of Ser. No. 121,993, Nov. 23, 1987, Pat. No. 4,976,954, which is a continuation-in-part of Ser. No. 937,196, Dec. 2, 1986, abandoned.

[51] Int. Cl.$^5$ .......................... A61K 7/16; A61K 7/18; A61K 7/30
[52] U.S. Cl. ......................................... 424/52; 424/48; 424/49; 424/55; 424/56; 424/57; 424/58; 424/464; 514/835; 514/901
[58] Field of Search ....................... 424/48, 49, 52, 55, 424/56, 57, 58, 464; 514/835, 901

[56] References Cited

U.S. PATENT DOCUMENTS

| | | | |
|---|---|---|---|
| 3,095,356 | 6/1963 | Moss | 424/49 |
| 3,864,472 | 2/1975 | Pensak et al. | 424/54 |
| 4,042,680 | 8/1977 | Muhler et al. | 424/55 |
| 4,108,979 | 8/1978 | Muhler et al. | 424/49 |
| 4,108,981 | 8/1978 | Muhler et al. | 424/49 |
| 4,146,605 | 3/1979 | Ritchey et al. | 424/49 |
| 4,153,732 | 5/1979 | Muhler et al. | 424/49 |
| 4,537,778 | 8/1985 | Clipper | 424/53 |
| 4,645,662 | 2/1987 | Nakashima et al. | 424/52 |

FOREIGN PATENT DOCUMENTS

| | | |
|---|---|---|
| 829272 | 12/1969 | Canada . |
| 871117706.9 | 4/1988 | European Pat. Off. . |
| 3610M | 10/1965 | France . |
| 200749 | 8/1953 | New Zealand . |
| 2004463 | 4/1979 | United Kingdom . |

OTHER PUBLICATIONS

R. S. Manly and B. G. Bibby, *J. Dent. Res.*, 28:160 (1948).
Regolati et al., *Helv. Odont. Acta*, 13:59 (1960).
Kelada, Nabih P., "Electrochemical Characteristics of Free and Complexed Fluorides in Drinking Water and the Effects of Aluminum and Iron on Fluoride Incorporation into Tooth Enamel", Univ. Michigan Thesis (1972).
Rosenthal, M. W., *Cosmetics: Science and Technology*, 2nd Ed., vol. 1; John Wiley & Sons, Inc., New York, NY 1977, Chapter 15, pp. 533-562.
C. J. Kleber and M. S. Putt, *Clinical Preventative Dentistry*, vol. 6, No. 6, 1984, pp. 14-25.
M. S. Putt and C. J. Kleber, *Journal of Dental Research*, Mar. 1985, pp. 437-439.
C. J. Kleber and M. S. Putt, *Journal of Dental Research*, Dec. 1985, pp. 1374-1376.
M. S. Putt and C. J. Kleber, *Journal of Dental Research*, Nov. 1986, pp. 1356-1358.
D. E. Gerhardt and A. S. Windeler, *Journal of Dental Research*, May-Jun. 1972, vol. 51, No. 3, p. 870.
H. G. McCann, *Archs. Oral Biol.*, vol. 14, pp. 521-531, 1969, "The Effect of Fluoride Complex Formation on Fluoride Uptake and Retention in Human Enamel".
Stedman's Medical Dictionary, 23rd ed., Williams & Wilkins Co., Baltimore, MD, p. 456 (1976).

*Primary Examiner*—Ronald W. Griffin
*Attorney, Agent, or Firm*—Barnes & Thornburg

[57] ABSTRACT

Improved anticariogenic oral preparations having a pH of about 2.5 to about 5.0 comprise an anticariogenically effective amount of a water-soluble aluminum salt in a surfactant-containing emulsion system suitable for use in the mouth.

11 Claims, No Drawings

ANTICARIOGENIC COMPOSITIONS

This application is a divisional of application Ser. No. 121,993 filed Nov. 23, 1987, now U.S. Pat. No. 4,976,954, which is a continuation-in-part of application Ser. No. 937,196 filed Dec. 2, 1986 (now abandoned).

BACKGROUND AND SUMMARY OF THE INVENTION

This invention relates to an oral preparation for use in the prevention of dental caries. More particularly, this invention relates to a stable, low-pH emulsion for oral administration as a dental caries prophylactic.

It has been found that aluminum salts can be used in a flavored emulsion with selected nonionic surfactants to produce a cariostatically active low-PH composition that is both stable and palatable to humans. The oral composition may be used in the preparation of a wide variety of products, including mouthwashes, chewing gums, prophylaxis pastes, dentifrices, dental rinses, and lozenges.

Anticariogenic preparations are well known in the art. Topical formulations containing fluoride, stannous fluoride, or sodium fluoride, for example, are known to provide partial protection against dental caries. Although effective dental caries protection has been obtained through the use of such fluoride-containing compounds, occasional side effects have been experienced with certain of the known fluoride-containing anticariogenic agents, particularly certain tin-containing salts. A brownish pigmentation has been noted after anticariogenic agents containing the stannous ion have been applied to the teeth. Although the pigmentation is not necessarily undesirable from a physiological standpoint, for aesthetic reasons, it would be desirable to provide an effective anticariogenic agent that does not discolor enamel.

The utility of fluoride materials has also been limited by the extent of their solubility and stability in aqueous media. For example, sodium fluoride is only soluble to the extent of about 4% in water. Furthermore, because of toxicity concerns, current regulations imposed by the U.S. Food and Drug Administration limit the amount of fluoride that can be provided in products sold for over-the-counter use.

For the foregoing and other reasons, dental researchers have continued their efforts to develop new anticariogenic agents which not only demonstrate a high level of anticariogenic effectiveness but are non-toxic, stable, and widely available. It has been suggested that aluminum salts may have a beneficial effect in reducing dental caries or in facilitating the uptake of fluoride by the dental enamel. See, e.g., Manly, et al., *J. Dent. Res.* 28: 160 (1948); Regolati, et al., *Helv Odont. Acta.* 13: 59 (1969); and Kelada, "Electrochemical Characteristics of Free and Complexed Fluorides in drinking Water and the Effects of Aluminum and Iron on Fluoride Incorporation Into Tooth Enamel," Univ. Michigan Thesis (1972).

In vitro studies have shown that pretreatment of enamel with aluminum solutions resulted in increased fluoride uptake when followed by treatment with a fluoride solution; however, treatment with combinations of aluminum and fluoride did not afford any added benefit over that of fluoride alone. McCann, *Arch. Oral Biol* 14:521 (1969); and Gerhardt, et al., *J. Dent Res* 51:870 (1972). The foregoing techniques dealt primarily with the use of aluminum in combination with fluorides and did not focus on the effect of aluminum in the absence of fluoride.

Nor has the use of aluminum salts in dentifrices demonstrated a desirable result, primarily because there has been but recent recognition that conventional dentifrice abrasives are incompatible with sources of biologically available aluminum (U.S. Pat. No. 4,108,979). While French Patent No. 3610M describes a specific combination of aluminum lactate, aluminum fluoride, and calcium pyrophosphate, the abrasive interferes with aluminum ion activity by forming insoluble aluminum phosphate. Similarly, U.S. Pat. No. 3,095,356 uses aluminum salts such as aluminum fluoride to coact with insoluble sodium metaphosphate abrasives to reduce the solubility of such abrasives and to increase fluoride uptake, but without independent therapeutic advantage being taken of the aluminum.

Canadian Pat. No. 829,272 describes acidic dentifrices comprising a combination of surface active substances and albumen-coagulating substances such as certain carboxylic acid salts of aluminum and other metals. However, this patent fails to teach that the satisfactory use of aluminum ions in dentifrices is dependent upon the use of aluminum compatible constituents, that is, constituents which when present in solution with aluminum ions, do not complex or react with them to render said ions unreactive with the surface of teeth.

U.S. Pat. No. 4,108,981 describes an alkaline mouthwash composition (pH 7-9) comprising aluminum salts and carboxylic acid. However, that patent teaches that the carboxylic acid is required to stabilize the aluminum in the mouthwash preparation. Similarly, U.S. Pat. No. 4,153,732 teaches that ascorbic and adipic acids can be used to stabilize an aluminum-containing comestible. It further teaches that, in fact, many carboxylic acids interfere with aluminum ions. (Column 5; lines 7-9). There is nothing to suggest the use of aluminum ions without a stabilizing acid, merely that certain carboxylic acids are more compatible with aluminum.

In sum, the prior art has not heretofore suggested a stable anticariogenic preparation of aluminum ions at low pH without the presence of carboxylic acids and/or fluoride. One of the main problems associated with the formulation of such aluminum ion preparations is that aluminum is naturally very astringent, tart-tasting, and produces a profound drying sensation in the oral cavity. Another problem is that aluminum is very reactive and can easily be inactivated by many conventional cosmetic ingredients.

An object of the present invention therefore is to provide a novel, low-pH composition for inhibiting dental caries employing aluminum in a compatible emulsion system.

A further object is to provide cariostatically effective aluminum-containing oral preparations which are both stable and palatable.

A still further object is to provide new anticariogenic emulsions useful for preparation of mouthwashes, dentifrices, chewing gums, lozenges, and prophylaxis pastes.

DETAILED DESCRIPTION OF THE INVENTION

The present invention is directed to anticariogenic aluminum-containing emulsions having a pH of about 2.5 to about 5.0 and adapted for application to teeth. The compositions comprise water-soluble aluminum salts in an amount sufficient to provide an anticariogenic concentration of aluminum ions in an aqueous emulsion stabilized with selected surfactants. Preferably for enhanced palatability the present compositions include, in addition, one or more substances selected from flavor oils, humectants and sweeteners.

Cariostatically active emulsions of this invention may be prepared by a variety of methods so long as aluminum ions are provided in an aqueous medium having a PH in the range of about 2.5 to about 5.0. At pH levels less than 2.5, the emulsion is generally too astringent-tasting, causes erosion of the teeth, and is generally not palatable. Above pH 5.0, substantially all of the aluminum is precipitated as aluminum hydroxide. A preferred pH range for the present formulation is about 3.0 to about 4.5, and more preferably about 3.5 to about 3.9.

The invention features water-soluble aluminum salts in an emulsion. The particular water-soluble aluminum salt employed is not critical, and substantially any non-toxic, water-soluble aluminum ion-containing salt may be used. Suitable water-soluble aluminum salts include aluminum potassium sulfate, aluminum chloride, aluminum sodium sulfate, aluminum sodium phosphate, aluminum sulfate, aluminum nitrate, sodium aluminate, and mixtures thereof. Other water-soluble aluminum salts are aluminum acetate, aluminum ammonium sulfate, aluminum bromate, aluminum bromide, aluminum chlorate, aluminum iodide, aluminum lactate, aluminum phenylsulfonate, and potassium aluminate. Aluminum potassium sulfate and aluminum chloride are preferred by reason of their wide availability and well-established safety. The aluminum salts are present in an amount sufficient to provide an emulsion having a concentration of available aluminum ions of about 10 to about 50,000 ppm, preferably about 250 to about 10,000 ppm and particularly for mouthwash formulations, most preferably about 500 ppm. "Available aluminum ions" for the purpose of defining this invention are aluminum ions capable of reacting or complexing with a substance of the teeth, including enamel, cementum and dentin. Aluminum ions which are complexed with anionic/-chelating substances exhibit little if any reactivity with tooth surfaces.

Representative humectant materials useful in this invention include glycerin, mannitol, sorbitol, xylitol and mixtures thereof. Glycerin is the preferred humectant on the basis of cost, availability, and ability to reduce the astringency of the aluminum. Humectant materials are present in the emulsion in an amount ranging from about 1 to about 90 percent by weight, preferably about 5 to about 60 percent by weight, and more preferably, about 5 to about 20 percent by weight. In mouthwash formulations, a humectant is typically used at about 10 percent by weight of the formulation.

The emulsion also includes a sweetening agent. Suitable sweeteners include sucrose, fructose, levulose, and dextrose, and mixtures thereof as well as noncariogenic artificial sweeteners such as saccharin, cyclamate and aspartame. Preferably a noncariogenic sweetener is employed in the oral composition of this invention.

Due to the astringent-tasting uncomplexed aluminum compounds, it is typically necessary to utilize a flavoring material to mask effectively the astringent taste. Representative flavoring oils include oils of wintergreen, peppermint, citrus, cassia, cherry, tutti frutti, raspberry, root beer, orange, grape, and other suitable flavor oils. The flavor oils are present in concentrations ranging from about 0.1 to about 5.0 percent by weight and preferably, about 0.2 to about 2.0 percent by weight. For most formulations, no more than about 1.0 weight percent flavor oil is required to obtain acceptable palatability.

The emulsions of this invention are predicated on the discovery that certain surfactants, especially nonionic hydrophilic surfactants, enable formulation of stable, low-pH, flavor oil-aqueous aluminum salt emulsions. The use of such aluminum-compatible surfactants enables the formulation of stable, aqueous systems containing high flavor oil levels, thereby eliminating the need of ethyl alcohol for flavor oil solubilization. Nonionic surfactants, in general, tend to decompose at alkaline PH. They are, however, quite stable under acidic conditions, as is the case for the aluminum compositions of this invention.

Certain classes of cationic and anionic surfactants have also been demonstrated to exhibit surprising compatibility and efficacy in the anticariogenic compositions of this invention. Thus aluminum ions have also been found to retain "activity" in the presence of art-recognized polyalkoxylated, e.g., polyethoxylated and polypropoxylated surfactants, particularly polyalkoxy carboxylates, polyalkoxy sulfates and polyalkoxylated amines. Polyalkoxylated anionic and cationic surfactants possess a sufficient and apparently dominant non-ionic character which manifests itself in an unexpected level of compatibility with cationic aluminum. Quarternary ammonium surfactants and amphoteric surfactants derived from the amino acids glycine, cysteine and phenylalanine have also exhibited acceptable compatibility with aluminum ions.

The surfactants used for an aluminum rinse in accordance with this invention are non-toxic and water-soluble, each preferably with a dominant hydrophilic moiety. The hydrophilic surfactants are nonionic or have the aluminum-compatible functionality of nonionic surfactants.

One suitable nonionic surfactant is a polyoxyethylene derivative of a sorbitan fatty acid ester and preferably, a sorbitan mono fatty ester. More preferably, the sorbitan mono fatty ester surfactant is a polyoxyethylene derivative of a sorbitan fatty acid ester wherein the ester-forming fatty acid is selected from lauric acid, palmitic acid, oleic acid, and stearic acid. A nonionic surfactant having the desired chemical properties is Tween* 20 from Atlas Chemical Industries, Inc. Chemically, it is a polyoxyethylene 20 sorbitan monolaurate. Another suitable surfactant manufactured by Atlas is SPAN* 80 sorbitan monooleate.

Another suitable nonionic surfactant is one selected from a class of block copolymers of propylene oxide and ethylene oxide. One such water-soluble, nontoxic, nonionic surfactant is Poloxamer 407 (tradename Pluronic* F127) from BASF Wyandotte Company. Its use is discussed in U.S. Pat. No. 3,864,472 entitled Clear Lemon-flavored Mouthwash. Chemically the Pluronics are block copolymers of propylene oxide and ethylene oxide containing various amounts of hydrophobe (polyoxypropylene) and hydrophile (polyoxyethylene). The Pluronic* F127 is characterized as a hydrophilic surfactant.

The surfactants and surfactant mixtures employed in this invention have a composite hydrophile-lipophile-balance (HLB) of between about 9 and about 30. Preferably, the sorbitan fatty acid ester is a polyoxyethylene derivative of sorbitan monolaurate having an HLB of about 9 to about 18, preferably about 17, and the block copolymer of propylene oxide and ethylene oxide has an HLB of about 15 to about 30, preferably about 22.

The block copolymer and the sorbitan fatty acid ester are preferably used in combination in a ratio of about 2:1 to about 200:1, and more preferably, in a ratio of about 4:1 to about 50:1. The present emulsions preferably contain about 0.1 to about 5 percent by weight sorbitan fatty acid ester and about 0.1 to about 20 percent by weight block copolymer of propylene oxide and ethylene oxide.

The emulsions of the present invention may also contain water-soluble, fluoride-containing, anticariogenic adjuvants. Preferably such an adjuvant is present in the form of water-soluble, fluoride-containing compounds capable of supplying fluoride ions. The preferred adjuvant is sodium fluoride, although other materials such as sodium monofluorophosphate, stannous fluorozirconate, indium fluorozirconate, stannous fluoride, and complex zirconium-germanium fluorides may be employed. Sodium fluoride is preferred by virtue of the absence of objectionable taste, lack of enamel pigmentation, the freedom from damage to gingival tissue, and by reason of anticariogenic effectiveness obtainable therewith. Other suitable adjuvants include water-soluble fluoride salts such as $NH_4F$, $SnF_4$, $KF$, $InF_3$, $PbF_2$, $FeF_2$, and $LiF$, as well as more complex water-soluble, fluoride-containing, adjuvants such as fluorosilicates, fluorozirconates, fluorostannites, fluoroborates, fluorotitanates, fluorogermanates, and mixed halides. Mixtures of suitable adjuvants may also be utilized. Aluminum fluoride may be used to supply both aluminum and fluoride to the system. In general, such fluoride adjuvants are present in anticariogenically effective and non-toxic amounts, typically at a level of about 0.05 up to about 1.0 percent by weight of the dentifrice preparation so as to provide up to about 1000 ppm fluoride ion.

The emulsions of this invention have demonstrated significant utility as anticariogenic agents for use in oral compositions comprising carriers such as water and other non-toxic materials. The compositions of this invention may be applied to teeth in aqueous solution of such carriers as in a topical treatment solution or in the form of a mouthwash. However, the compositions of the present invention are also well-suited for formulation of other oral compositions for dental caries prophylaxis, e.g., dentifrices and prophylaxis pastes/gels containing one or more compatible abrasives, lozenges, and chewing gums. Indeed, substantially any carrier capable of supplying active aluminum agent to the surface of the teeth may be employed in accordance with this invention.

In a preferred embodiment of the present invention, the emulsion is formed by mixing an aqueous solution of the aluminum salts with a sweetener and a blocked copolymer of propylene oxide and ethylene oxide. A second mixture of a polyoxyethylene derivative of a sorbitan fatty acid ester, flavor oil, and glycerin is prepared. The first and second mixtures are thereafter blended to form an emulsion of the present invention.

Emulsions of this invention are employed at their natural pH values, which range from about 2.5 to about 5.0 due to the Lewis acid effect of the aluminum. In a preferred embodiment, the pH of the emulsion ranges from about 3.5 to about 3.8. In all cases, the ingredients provided in the emulsions of this invention are selected so as to be compatible with aluminum ions.

Exemplary preparations employing the oral compositions of the present invention are given in the following Examples 1-5.

EXAMPLE 1

| MOUTHWASH PREPARATION | |
|---|---|
| Ingredients | % By Weight |
| Distilled water | 85.070 |
| Pluronic* F127 (BASF Wyandotte) | 3.000 |
| $AlK(SO_4)_2 \cdot 12H_2O$ | 0.885 |
| Sodium saccharin | 0.100 |
| Glycerin | 10.000 |
| Tween* 20 (ICI Americas) | 0.600 |
| Flavor oil | 0.300 |
| 5% solution F D & C yellow dye #4 | 0.040 |
| 5% solution F D & C blue dye #1 | 0.005 |
| | 100.000% |

EXAMPLE 2

| DENTIFRICE PREPARATION | |
|---|---|
| Ingredients | % By Weight |
| Abrasive | 32.00 |
| Water | 20.31 |
| Glycerin | 17.50 |
| Sorbitol (70%) | 14.00 |
| NaOH (33⅓%) | 1.00 |
| Binder | 1.00 |
| Pluronic F-87 | 9.00 |
| $AlK(SO_4)_2 \cdot 12H_2O$ | 3.54 |
| Sodium saccharin | 0.25 |
| Tween 20 | 0.80 |
| Cassia flavor | 0.40 |
| Methyl paraben | 0.15 |
| Prophyl paraben | 0.05 |
| | 100.00 |

EXAMPLE 3

| LOZENGE PREPARATION | |
|---|---|
| Ingredients | % By Weight |
| Sorbitol (70%) | 97.9 |
| Pluronic F-127 | 1.2 |
| $AlCl_3 \cdot 6H_2O$ | 0.5 |
| Tween 80 | 0.2 |
| Flavorings, color, etc. | 0.2 |
| | 100.0 |

EXAMPLE 4

| CHEWING GUM PREPARATION | |
|---|---|
| Ingredients | % By Weight |
| Gum Base | 26.0 |
| Sorbitol powder | 47.9 |
| Sorbitol (70%) | 17.3 |
| Glycerin | 4.5 |
| Pluronic F-127 | 2.0 |
| Tween 60 | 0.1 |
| $AlK(SO_4)_2 \cdot 12H_2O$ | 1.0 |
| Flavoring | 1.2 |
| | 100.0 |

EXAMPLE 5

| PROPHYLAXIS PASTE PREPARATION | |
|---|---|
| Ingredients | % By Weight |
| Abrasive | 48.0 |
| Water | 14.0 |
| Glycerin | 10.0 |
| Sorbitol (70%) | 6.0 |
| NaOH (33⅓%) | 2.0 |
| Binders | 1.5 |
| Pluronic - F88 | 8.0 |
| Al(NO$_3$)$_3$·9H$_2$O | 7.0 |
| Tween 80 | 1.0 |
| Sweeteners, flavor, etc. | 2.5 |
| | 100.0% |

EXPERIMENTAL EVALUATION

Rat Dental Caries Study

The significant anticariogenic benefits of the aluminum-containing emulsion of this invention have been demonstrated in a dental caries study performed with rats.

The rat dental caries model used was that recommended by the National Institute of Dental Research NIH, (Larson, R. H. et al., *J. Dent. Res.*, 56:1007–1012, 1977). The study was designed to examine the effect of two experimental aluminum-containing dental rinses (Groups 3 and 4) on dental caries formation in the albino rat. The aluminum rinses were compared to a positive control fluoride rinse (Group 5) and two negative control cells consisting of water (Group 1) and a placebo rinse (Group 2). Furthermore, since aluminum has been demonstrated to enhance the effect of fluoride, a double treatment group (Group 6) was included in which the animals were treated first with aluminum followed by fluoride Twenty litters of eight weanling Wistar strain rats were randomly distributed into eight equal groups of 20 animals according to sex, body weight, and litter mates. The rats were weighed initially, at one month, provided with NIDR cariogenic diet 2000 and distilled drinking water for the ten-week study.

All weanling rats initially were inoculated with the caries-inducing microorganisms, Streptococcus mutans 6715. The molars of the rats were swabbed with a 24-hour culture of the S. mutans 6715 and the residual was placed in their drinking water at a 1:100 dilution. The inoculations were repeated for 3 consecutive days to insure implantation of the microorganism.

The formulae for preparation of the dental rinse solutions used for treatment Groups 2–5 in the study are set forth in Table 1.

TABLE 1

Dental Rinse Formulae for Rat Dental Caries Study

Percentage by Weight

| Ingredients | Group 2 Placebo | Group 3 AlK(SO$_4$)$_2$ | Group 4 AlCl$_3$ | Group 5 NaF |
|---|---|---|---|---|
| Distilled water | 85.955 | 84.177 | 85.062 | 85.800 |
| Pluronic* F127 | 3.000 | 3.000 | 3.00 | 3.000 |
| Aluminum potassium sulfate dodecahydrate | — | 1.758 | — | — |
| Aluminum chloride hexahydrate | — | — | 0.893 | — |
| Sodium fluoride | — | — | — | 0.155 |
| Sodium saccharin | 0.100 | 0.100 | 0.100 | 0.100 |
| Glycerin | 10.000 | 10.000 | 10.000 | 10.000 |
| Tween* | 0.600 | 0.600 | 0.600 | 0.600 |
| Citrus flavor | 0.300 | 0.300 | 0.300 | 0.300 |
| FD&C yellow dye #4 (5% solution) | 0.040 | 0.040 | 0.040 | 0.040 |
| FD&C blue dye #1 (5% solution) | 0.005 | 0.005 | 0.005 | 0.005 |
| Sodium hydroxide (33⅓%) | — | q.s. | q.s. | — |
| Final pH | 6.5 | 3.8 | 3.8 | 6.5 |

The dental rinse solutions were prepared in accordance with the following procedure. The aluminum salt (or NaF) was first dissolved in 90% of the water with stirring. The sodium saccharin was then dissolved in the solution, following by the Pluronic* F127 surfactant. The solution was stirred for about one hour to totally dissolve the Pluronic* F127. The Tween* 20 and flavor oil were mixed in a separate container and the glycerin was subsequently added to and mixed with the flavor-oil Tween* 20 solution. The oil-surfactant mixture was slowly added to the aqueous mixture with stirring to form a clear emulsion. Coloring dyes were then added to the dental rinses. The pH of the aluminum rinses was slowly adjusted to 3.8 with the sodium hydroxide. The rinses were quantitatively transferred to a volumetric container of appropriate size, filled with the remaining distilled water, and used throughout the entire study.

Each hemijaw of each rat was swabbed for 15 seconds with the respective dental rinse twice daily, five days per week. The group treatment sequence was varied each day in order to minimize any potential error due to time of day of treatment.

After final weighing, the treated rats were sacrificed in pairs by chloroform inhalation and decapitated. The mandibles and maxillas were then surgically removed and defleshed in preparation for caries scoring. All animals were coded to prevent identification of the treatment vs. control groups by the examiner.

Dental caries was determined by scoring the number and severity of carious areas in sectioned teeth. The mandibles and maxillas were soaked overnight in an aqueous 0.05% ammonium purpurate (Murexide) solution to stain the decayed enamel. The buccal, lingual, and morsal surfaces were scored using a binocular dissection microscope and the location and size of lesions recorded on individual caries scoring charts. The hemijaws were subsequently sectioned mesially-distally into halves and graded for sulcal and proximal lesions.

The dental caries results are summarized in Table 2. This table includes the average final weight, smooth surface caries, and fissure caries scores, the percent reductions, and the statistical results. The smooth surface caries data, which are a combination of the buccal, lingual, and proximal lesion scores, represent the amount of dental decay observed on the outer surfaces of the rat teeth. The results demonstrated that the AlCl$_3$, AlK(SO$_4$)$_2$, and NaF rinses (Groups 3, 4, and 5, respectively) significantly reduced smooth surface dental caries by 43, 37, and 37%, respectively.

Numerically, the best reduction in smooth surface caries was observed for Group 6, which received the dual phase treatment of AlCl$_3$ and NaF. Although the 51% reduction observed for this double treatment group was significantly different from the controls, it was not statistically better than the 37% reductions observed for the individual NaF or AlCl$_3$ treatments fluoride during the study. This necessitated: (1) conducting the study in an area where there was minimal fluoride content in the drinking water and (2) providing the children in Group 2 with a non-fluoride dentifrice.

TABLE 2

SUMMARY OF RAT DENTAL CARIES STUDY

| | | | | Final Wt. (gm) | | Smooth Surface Caries | | | Fissure Caries | | |
|---|---|---|---|---|---|---|---|---|---|---|---|
| Group | Treatment[a] | pH | n | Score[b] | Sig.[c] | Score[b] | Red.[c] | Sig.[c] | Score[b] | Red.[c] | Sig.[c] |
| 1 | Distilled water | 6.5 | 20 | 239 | none | 11.10 | — | 3,4,5,6 | 24.45 | — | 3,4,5,6 |
| 2 | Placebo | 6.5 | 20 | 241 | none | 11.40 | — | 3,4,5,6 | 26.80 | — | 3,4,5,6 |
| 3 | AlK(SO$_4$)$_2$ | 3.8 | 20 | 241 | none | 6.45 | 43% | 1,2 | 17.35 | 35% | 1,2,5,6 |
| 4 | AlCl$_3$ | 3.8 | 20 | 246 | none | 7.20 | 37% | 1,2 | 17.35 | 35% | 1,2,5,6 |
| 5 | NaF | 6.5 | 20 | 237 | none | 7.15 | 37% | 1,2 | 7.45 | 72% | 1–4 |
| 6 | AlCl$_3$ & NaF | — | 20 | 242 | none | 5.55 | 51% | 1,2 | 6.75 | 75% | 1–4 |

[a]All active agents present at a concentration of 0.037 Molar
[b]Mean value, n = 20
[c]The numbers represent the treatment groups which are significantly different according to the Newman-Keuls statistical test.

(Groups 4 and 5, respectively). However, these data seem to indicate that aluminum may enhance the effect of fluoride.

The fissure caries results also summarized in Table 2 are a combination of the sulcal and morsal lesions and represent the amount of dental decay observed in the pit and fissure areas of the rat molars. The results demonstrated that AlCl$_3$ and AlK(SO$_4$)$_2$ (Groups 3 and 4), significantly reduced the number of fissure caries by 35% each. NaF (Group 5) significantly reduced fissure caries by 72%. Group 6, treated first with AlCl$_3$, and then NaF, resulted in the greatest reduction in fissure caries of 75%.

The overall results demonstrated that the ingredients used to formulate the dental rinse vehicle did not inactivate the aluminum or fluoride and did not possess any anticariogenic properties themselves. The rats in all six groups exhibited consistent and equivalent weight gains. This, coupled with the fact that no deaths occurred during the ten-week study period, provided further evidence regarding the lack of toxicity of aluminum. Thus, the dental rinse formulation was safe and effective to use as a vehicle for administering the aluminum in the human dental caries clinical study.

Human Dental Caries Clinical Investigation

A human clinical investigation was undertaken to determine the effectiveness of a topically-applied aluminum dental rinse prepared in accordance with the subject invention in reducing the incidence of dental caries compared with a positive control fluoride dentifrice. AlK(SO$_4$)$_2$ was used in the human dental caries study because of its GRAS (generally regarded as safe) status with the U.S. Food and Drug Administration.

A total of 260 elementary school children having a high incidence of caries was selected from three schools located in a low-fluroide area (0.4 ppm F or less in the water supply). All children who were caries-free or had fissure sealants or orthodontic appliances were excluded. This precaution minimized the natural interference and variability these factors introduce into a dental caries clinical study. The children were examined both clinically and radiographically for dental caries and stratified into three groups. Group 1 served as the positive control and received a fluoridated dentifrice approved by the American Dental Association. Group 2 was given an experimental dental rinse containing 0.81% aluminum potassium sulfate with the pH adjusted to 3.8. In order the examine the anticariogenic effect of aluminum, it was essential that the subjects in Group 2 were not exposed to any exogenous sources of fluoride during the study. This necessitated: (1) conducting the study in an area where there was minimal fluoride content in the drinking water and (2) providing the children in Group 2 with a non-fluoride dentifrice.

Group 3 received the same rinse as Group 2, but was supplied with the same fluoride dentifrice as Group 1 in order to examine the synergistic effect of aluminum and fluoride. For ethical reasons there was no placebo. The experimental groups were compared to the fluoride dentifrice positive group.

The dental rinses were self-administered under direct supervision at school after the noon meal, 5 days per week. When school was not in session, the rinses were self-applied at home under parental supervision. The procedure consisted of rinsing for 30 seconds each day with 10 ml of the dental rinse. After one month, the children were examined for gingivitis, mucosal irritations, enamel decalcification, etc., but no significant side effects were observed.

After six months, the children were again examined clinically and radiographically for dental caries. Because all groups exhibited a significant or directionally positive effect at the six-month examination, the study was allowed to continue for a one-year examination period. At all times the double-blind status of the test was maintained. Examiner efficiency was maintained by scheduling reasonable numbers of examinations per session with adequate rest periods.

The dental rinses were as similar in appearance and taste as possible and were formulated in a form most palatable to children. The particular flavor of the rinses were changed periodically to provide variety and to maintain interest. Each batch was checked for enamel solubility reduction (ESR) in the laboratory before distribution in order to ensure cariostatic activity of the formulation.

The ESR tests were performed using the method described by Putt and Kleber (J. Dent. Res., 64:437–440, 1985).

Table 3 presents the ESR data for the six various flavored aluminum rinses utilized in the clinical study. Enamel dissolution by acid was reduced by approximately 70% after treatment with the aluminum dental rinses. The data indicated that all the aluminum-containing formulations were highly active and no significant incompatibilities occurred between aluminum and the other dental rinse ingredients. Placebo formulations without aluminum demonstrated no effect whatsoever in reducing enamel solubility, verifying that the aluminum was the active component.

Participants in Group 1 and 3 received adequate supplies of toothbrushes and a standard fluoride dentifrice (Crest*) repackaged in unmarked white tubes to use at home according to their normal oral hygiene habits. Participants in Group 2 were supplied in like manner with a standard non-fluoride dentifrice (Pepsodent*).

Examinations were performed by two dentists experienced in conducting dental caries studies. The techniques employed in the dental caries examinations were those recommended by the 1955 A.D.A. Dental Caries Symposium, the Ohio State Symposium, the 1961 Zurich Caries Symposium, and the 1968 A.D.A. Conference on the Clinical Testing of Cariostatic Agents.

The six-month results for the aluminum rinse dental caries study are presented in Table 4. These results demonstrated clinically that aluminum is effective in reducing dental caries in humans.

TABLE 4

DENTAL CARIES INCREMENTS AFTER SIX MONTHS

| | Treatment | | | DMFT | | | | DMFS | | | |
|---|---|---|---|---|---|---|---|---|---|---|---|
| Group | Rinse | Dentifrice | N | Mean | SEM[c] | % Red | Sig | Mean | SEM[c] | % Red | Sig |
| | | | | | Examiner A | | | | | | |
| 1 | Placebo | Fluoride[a] | 77 | 1.00 | 0.162 | — | — | 1.62 | 0.268 | — | — |
| 2 | Aluminum[b] | Placebo | 80 | 0.58 | 0.168 | 42% | p = .04 | 1.04 | 0.265 | 36% | p = .06 |
| 3 | Aluminum[b] | Fluoride[a] | 80 | 0.59 | 0.140 | 41% | p = .03 | 0.89 | 0.215 | 45% | p = .02 |
| | | | | | Examiner B | | | | | | |
| 1 | Placebo | Fluoride[a] | 77 | 0.75 | 0.141 | — | — | 1.22 | 0.233 | — | — |
| 2 | Aluminum[b] | Placebo | 80 | 0.57 | 0.136 | 24% | p = .18 | 0.92 | 0.200 | 25% | p = 0.16 |
| 3 | Aluminum[b] | Fluoride[a] | 80 | 0.67 | 0.154 | 10% | p = .35 | 0.97 | 0.220 | 21% | p = 0.22 |

[a] Crest ® With Fluoristat; contains 1100 ppm F as NaF
[b] Contains 500 ppm $Al^{+3}$ as $AlK(SO_4)_2 \cdot 12 H_2O$, pH 3.8
[c] Standard error of the mean

TABLE 3

REDUCTION IN ENAMEL SOLUBILITY BY VARIOUS FLAVORED DENTAL RINSES USED IN HUMAN CLINICAL STUDY

| Dental Rinse[a] | | | | Enamel Solubility |
|---|---|---|---|---|
| Active Agent | Flavor | pH | n | Reduction Score[b] |
| 0.885% $AlK(SO_4)_2 \cdot 12H_2O$ | 0.3% citrus-mint | 3.8 | 3 | 74 ± 3 |
| 0.885% $AlK(SO_4)_2 \cdot 12H_2O$ | 0.075% cassia | 3.8 | 6 | 71 ± 1 |
| 0.885% $AlK(SO_4)_2 \cdot 12H_2O$ | 0.3% lemon | 3.8 | 4 | 63 ± 2 |
| 0.885% $AlK(SO_4)_2 \cdot 12H_2O$ | 0.3% grape | 3.8 | 6 | 64 ± 3 |
| 0.885% $AlK(SO_4)_2 \cdot 12H_2O$ | 0.3% pineapple | 3.8 | 6 | 69 ± 4 |
| 0.885% $AlK(SO_4)_2 \cdot 12H_2O$ | 0.3% strawberry | 3.8 | 6 | 72 ± 3 |
| None | 0.075% cassia | 6.8 | 3 | −7 ± 5 |
| None | 0.3% lemon | 6.8 | 3 | −8 ± 9 |

[a] All rinses prepared according to formula in Example 1, except for the pineapple flavor in which 1.2% Tween 20 was used.
[b] Mean ± standard error During the examination procedures neither the examiners nor the trained recorder had knowledge of the previous diagnosis or the group assignments. Two film bite-wing radiographs were obtained immediately following the clinical examination. The radiographs were developed on-site and retakes obtained as needed.

The subjects were randomly assigned to the study groups after stratification based on dental caries susceptibility, dental age, and past dental caries experience. Control and test subjects were examined in random order. Only permanent teeth were included in the examination and diagnostic findings were recorded by teeth and surfaces. When lesions had been restored, they were recorded. Extracted teeth were recorded as were erupted noncarious teeth. Visual dental caries examination findings were called out in code to a trained recorder who wrote the information on an individual patient chart for each clinical examination.

The clinical dental caries findings were expressed in terms of the average increase in the number of decayed, missing, and filled teeth (DMFT) and surfaces (DMFS) per person in each group. The various components of each index, and the distribution on the various surfaces (occlusal, buccal-lingual, and proximal) were also obtained. A separate category was tabulated for teeth erupting during the study.

The data in Table 4 demonstrate the differences (W) in decayed, missing, and filled teeth (DMFT) and surfaces (DMFS) observed by both examiners after six months. The results for Examiner A demonstrated that: (1) a 30-second rinse with a 500 ppm aluminum solution five days per week reduced the DMFT and DMFS significantly better than daily use of a positive control fluoride dentifrice by 42% and 36%, respectively; and (2) the use of the aluminum rinse in combination with fluoride dentifrice resulted in similar statistically significant reductions in DMFT and DMFS of 41% and 45% respectively, compared to the fluoride dentifrice positive control group. The results of Examiner B likewise demonstrated that the two aluminum rinse groups reduced dental caries better than the fluoride positive control group.

The increments in DMFT and DMFS observed by both examiners after one year are presented in Table 5. The results confirmed the 6-month data that aluminum is effective in reducing dental caries in humans. For the most part, the results paralleled the findings for both examiners at six months. The results for Examiner A demonstrated that: (1) the 500 ppm aluminum dental rinse reduced WDMFT and WDMFS significantly better than daily use of a positive control fluoride dentifrice by 38% and 40% respectively; and (2) the use of aluminum rinse in combination with fluoride dentifrice resulted in similar statistically significant reductions in WDMFT and WDMFS of 32% and 32%, respectively, compared to the fluoride dentifrice positive control group. Thus, the significant caries reductions for aluminum observed by Examiner A at six months were still apparent after one year.

TABLE 5

DENTAL CARIES INCREMENTS AFTER ONE YEAR

| | Treatment | | | DMFT | | | | | DMFS | | |
|---|---|---|---|---|---|---|---|---|---|---|---|
| Group | Rinse | Dentifrice | N | Mean | SEM[c] | % Red | Sig | Mean | SEM[c] | % Red | Sig |
| | | | | | | Examiner A | | | | | |
| 1 | Placebo | Fluoride[a] | 78 | 1.33 | 0.21 | — | — | 2.15 | 0.35 | — | — |
| 2 | Aluminum[b] | Placebo | 79 | 0.83 | 0.19 | 38% | $p = .04$ | 1.29 | 0.28 | 40% | $p = .04$ |
| 3 | Aluminum[b] | Fluoride[a] | 77 | 0.91 | 0.16 | 32% | $p = .06$ | 1.47 | 0.28 | 32% | $p = .06$ |
| | | | | | | Examiner B | | | | | |
| 1 | Placebo | Fluoride[a] | 78 | 1.12 | 0.17 | — | — | 1.90 | 0.26 | — | — |
| 2 | Aluminum[b] | Placebo | 79 | 1.04 | 0.17 | 7% | $p = 0.37$ | 1.59 | 0.24 | 16% | $p = 0.19$ |
| 3 | Aluminum[b] | Fluoride[a] | 77 | 1.06 | 0.19 | 5% | $p = 0.40$ | 1.66 | 0.32 | 13% | $p = 0.28$ |

[a] Crest ® With Fluoristat; contains 1100 ppm F as NaF
[b] Contains 500 ppm $Al^{+3}$ as $AlK(SO_4)_2 \cdot 12H_2O$, pH 3.8
[c] Standard error of the mean The results of Examiner B likewise demonstrated that the two aluminum rinse groups reduced dental caries better than the fluoride positive control group. However, all the percentage reductions were slightly less than Examiner A. This is believed to have resulted from the fact that Examiner B was not as critical as Examiner A in scoring incipient dental caries. The lack of additional cariostatic benefit for aluminum after one year was probably the result of the low decay rate during the second six-month period and the reduced usage of the aluminum rinses by the subjects due to unsupervised rinsing during the summer vacation period.

Table 6 lists the number of reversals in dental caries observed in each group for both examiners at the six-month and one-year examinations, which is indicative of remineralization or "healing" of incipient lesions. In all cases the two aluminum rinse groups results in a much greater number of reversals and of subjects with reversals than in the fluoride positive control. This was a very significant finding because it is known that fluoride is effective in remineralizing incipient lesions. Thus, reversals would be expected for the fluoride positive control. A greater percentage of the reversals was noted in the two aluminum groups for both examiners after both six and twelve months. For Examiner A, a greater percentage of subjects in the fluoride positive control group exhibited an increase in dental caries compared to the two aluminum groups.

Table 7 presents the number and percentage of subjects having caries-free permanent dentition during the course of the study. The number of subjects in the fluoride control group declined by one-half, while essentially no change was observed in the number of caries-free subjects in the two aluminum groups.

To investigate the possible cariostatic mechanism of aluminum, the clinical data for Examiner A were reanalyzed in three different ways: (1) the dental caries data for each group were broken down into subcategories with respect to tooth location and tooth surface type; (2) the new permanent teeth erupting during the study were examined for caries developing in each group; and (3) the reversal data for each group were subcategorized with respect to tooth location and surface.

This analysis indicated that the greatest caries protection afforded by the aluminum rinses occurred on the buccal surfaces of the posterior teeth (although the overall decay rate for buccal surfaces was not that high compared to the occlusal and interproximal surfaces). Because the children held the aluminum rinse predominantly between their cheeks and the buccal surfaces of the posterior teeth while mouth rinsing, it is consistent that the buccal surfaces exhibited the greatest reduction in decay because of the longer contact time with the aluminum.

In general, the aluminum rinse provided its second

TABLE 6

SUMMARY OF CHANGES IN DENTAL CARIES IN THE STUDY POPULATION

| | | | Percent Change in Dental Caries of Study Population | | | | | | | | | |
|---|---|---|---|---|---|---|---|---|---|---|---|---|
| | | | Six Months | | | | | | One Year | | | |
| | | | Examiner A | | | Examiner B | | | Examiner A | | | Examiner B | | |
| Group | Rinse | Dentifrice | Rev. | NC. | Inc. | Rev. | NC. | Inc. | Rev. | NC. | Inc. | Rev. | NC. | Inc. |
| 1 | Placebo | Fluoride | 12% | 26% | 62% | 12% | 38% | 51% | 10% | 24% | 65% | 4% | 36% | 60% |
| 2 | Aluminum | Placebo | 19% | 36% | 45% | 20% | 24% | 56% | 15% | 35% | 49% | 11% | 27% | 62% |
| 3 | Aluminum | Fluoride | 19% | 34% | 48% | 13% | 40% | 48% | 14% | 30% | 56% | 13% | 32% | 56% |

Rev. = Reversal in Dental Caries
NC. = No Change in Dental Caries
Inc. = Increase in Dental Caries greatest cariostatic effect on the occlusal surfaces com-

TABLE 7

NUMBER OF CARIES-FREE SUBJECTS OF EACH EXAMINATION

| | | | Caries-Free Subjects | | | | | | | | | |
|---|---|---|---|---|---|---|---|---|---|---|---|---|
| | | | Examiner A | | | | | | Examiner B | | | | | |
| | Treatment | | Initial | | 6-Month | | 1-Year | | Initial | | 6-Month | | 1-Year | |
| Group | Rinse | Dentifrice | N | (%) | N | (%) | N | (%) | N | (%) | N | (%) | N | (%) |
| 1 | Placebo | Fluoride | 10 | (12%) | 8 | (10%) | 6 | (8%) | 15 | (17%) | 8 | (10%) | 7 | (9%) |
| 2 | Aluminum | Placebo | 9 | (10%) | 7 | (9%) | 8 | (10%) | 14 | (16%) | 8 | (10%) | 8 | (10%) |
| 3 | Aluminum | Fluoride | 7 | (8%) | 5 | (6%) | 6 | (8%) | 11 | (13%) | 8 | (10%) | 9 | (12%) | pared to the fluoride positive control. Ordinarily fluoride provides the least effect on the occlusal surfaces. Consequently, administration of aluminum in a chewing gum vehicle may enable even more prolonged contact with the occlusal surfaces, thus providing a means of protecting an area that is both very susceptible to decay and generally unprotected by fluoride.

The aluminum rinse also provided a good effect interproximaly, but had a minimal effect on the lingual surfaces. However, the lingual surfaces likewise developed minimal dental caries.

Analysis of dental decay developing in the new permanent teeth that erupted during the course of the study demonstrated that very few of the newly erupted teeth in all three groups became carious. After one year only 10% of the newly erupted teeth in the fluoride positive control exhibited any decay on their surfaces. Even a lesser amount of decay (5% to 1%) was observed for the two aluminum groups. The predominant location for new carious development was the posterior occlusal surface. It appears that the aluminum-fluoride dual treatment may provide its greatest effect on newly erupting teeth.

Further analysis of the number and locations of reversals in DMFS occurring after six months and one year demonstrated that the majority of reversals occurred in the posterior dentition, predominantly with respect to the occlusal and interproximal surfaces. Moreover, the two aluminum rinse groups resulted in approximately twice as many reversals as fluoride in these two locations, especially in the interproximal locations. It therefore appears that aluminum provides greater remineralization of incipient lesions in those two surfaces most susceptible to dental decay.

The one-year dental caries clinical study demonstrated that aluminum in an acidic (PH 3.8) mouthwash emulsion, formed without use of stabilizing carboxylic acids, is a safe and effective agent in reducing the incidence of dental caries in humans. The study has given a strong indication that aluminum is actually superior to fluoride in cariostatic potential. Moreover, in this clinical study the odds were in favor of the Crest dentifrice fluoride positive control. It was probably used more than the aluminum rinse (daily versus 4-5 times per week), it contained more cariostatic agent (1100 ppm F versus 500 ppm $Al^{+3}$), and it has been clinically proven to prevent dental decay by 40%, compared to the approximately 25% reductions noted for most other commercial fluoride dentifrices.

Surfactant Compatibility Study

Representative samples of surfactants from common chemical subclasses within each class (anionic, nonionic, cationic, and amphoteric) of surfactants were selected and examined for their effect on enamel solubility reduction (ESR) using the procedure described by Applicants in *J. Dent. Res.*, 64:437-440 (1985). Results from these studies are presented in Tables 8 and 9.

TABLE 8
ESR, pH, AND VISUAL APPEARANCE OF ANIONIC, NONIONIC, CATIONIC, AND AMPHOTERIC SURFACTANTS

| TYPE OF SURFACTANT | EXAMPLE TESTED | TRADE NAME | SOURCE | SURFACTANT 1% CONC. pH SOL. | CALCIUM ESR 1 PTD MN | CALCIUM ESR 1 PTD SD | CALCIUM ESR 4 PTD MN | CALCIUM ESR 4 PTD SD | PHOSPHORUS ESR 1 PTD MN | PHOSPHORUS ESR 1 PTD SD | PHOSPHORUS ESR 4 PTD MN | PHOSPHORUS ESR 4 PTD SD |
|---|---|---|---|---|---|---|---|---|---|---|---|---|
| CONTROL | distilled water | none | stock | | 2 | 7 | −6 | 6 | 14 | 17 | −2 | 18 |
| I. ANIONIC | | | | | | | | | | | | |
| A. Carboxylates | | | | | | | | | | | | |
| 1. regular | sodium stearate | none | stock | 10.7 cl, fm | 10 | 7 | −17 | 8 | 13 | 9 | −19 | 9 |
| 2. polyalkoxycarboxylates | | Sandopan MS-40 | Sandoz | 6.1 tr | 8 | 8 | −4 | 1 | 2 | 2 | −4 | 1 |
| B. N-Acylsarcosinates | Na lauryl sarcosine | Hamposyl L | WR Grace | 3.3 i,ppt.26 | 8 | 8 | 8 | 20 | 10 | 5 | 4 | |
| | Na lauryl sarcosinate | Hamposyl L.30 | WR Grace | 6.6 tr | 12 | 10 | −25 | 14 | 4 | 10 | −27 | 7 |
| C. Acylated Protein Hydrolysates | none | none | | | | | | | | | | |
| D. Sulfonates | | | | | | | | | | | | |
| 1. alkylbenzenesulfonates | | Conco AAS-45S | Con Chem | | | | | | | | | |
| 2. alkylarenesulfonates | | | | | | | | | | | | |
| 3. lignosulfonates | | | | | | | | | | | | |
| 4. naphthalenesulfonates | | Daxad 11 | WR Grace | 6.6 tr | −4 | 2 | 2 | 10 | −7 | 2 | −1 | 8 |
| 5. a-olefinsulfonates | | Conco AOS-40 | Con Chem | | | | | | | | | |
| 6. petroleum sulfonates | | | | | | | | | | | | |
| 7. dialkylsultosuccinates | | Aerosol OT | Am Cyn | 5.7 tr | −4 | 7 | −3 | 14 | −6 | 10 | −7 | 13 |
| 8. amidosulfonates | | Concogel | Con Chem | | | | | | | | | |
| 9. acyl isethionates | | Dowfax 2A1 | Dow Chem | 7.5 tr | 1 | 2 | −8 | 3 | −2 | 3 | −11 | 1 |
| E. Sulfates and Sulfonated Products | | | | | | | | | | | | |
| 1. alcohol sulfates | Na lauryl sulfate | stock | stock | 8.0 tr, fm | −3 | 14 | −18 | 10 | −3 | 10 | −21 | 12 |
| 2. ethoxylated alcohol sulfates | | Conco Sulfate-219 | Con Chem | | | | | | | | | |
| 3. ethoxylated alkylphenol sulfates | | Triton X-301 | Rohm/Haas | 6.7 tr | −1 | 6 | −10 | 9 | 1 | 4 | −13 | 7 |
| 4. sulfated acids, amides, & esters | | | | | | | | | | | | |
| 5. sulfated oils & fats | | | | | | | | | | | | |
| F. Phosphate Esters | Na nonoxynol-6 phosphate | Emphos CS-1361 | Witco | | | | | | | | | |
| II. NONIONIC | | | | | | | | | | | | |
| A. Ethoxylates | | | | | | | | | | | | |
| 1. alcohol ethoxylates | alkylated polyether alcohol | Brig 35 | ICI Amer | 3.6 tr | 17 | 1 | −6 | 13 | 21 | 1 | −5 | 13 |
| | | Triton X-100 | Rohm/Haas | 4.1 tr, fm | 8 | 7 | −5 | 12 | 7 | 6 | −5 | 14 |
| 2. alkylphenol ethoxylates | | Igepal CO-660 | GAF Co | 6.6 tr | 26 | 1 | −3 | 6 | 24 | 1 | −7 | 10 |
| B. Carboxylic (Fatty) Acid Esters | | | | | | | | | | | | |
| 1. glycerol esters | glycerol monostearate | Adacel 165 | ICI Amer | | | | | | | | | |
| | glycerol & polyoxy-ethylene stearate | Arlacel 165 | ICI Amer | 4.7 v cl | −5 | 7 | −15 | 9 | −7 | 7 | −18 | 7 |
| 2. polyoxyethylene esters | | Myrj 525 | ICI Amer | 6.1 tr | −1 | 6 | −2 | 4 | −2 | 6 | −7 | 5 |
| | polyoxyethylene 20 isohexadecyl ether | Arlasolve 200 | ICI Amer | 4.1 tr | 2 | 8 | −6 | 8 | 1 | 8 | −7 | 7 |
| 3. anhydrosorbitol esters | | Span 20 | ICI Amer | 5.7 cl | −3 | 5 | −14 | 9 | −3 | 4 | −13 | 6 |
| | | Span 40 | ICI Amer | | | | | | | | | |

TABLE 8-continued
ESR, pH, AND VISUAL APPEARANCE OF
ANIONIC, NONIONIC, CATIONIC, AND AMPHOTERIC SURFACTANTS

| TYPE OF SURFACTANT | EXAMPLE TESTED | TRADE NAME | SOURCE | SURFACTANT 1% CONC. pH SOL. | CALCIUM ESR 1 PTD MN | CALCIUM ESR 1 PTD SD | CALCIUM ESR 4 PTD MN | CALCIUM ESR 4 PTD SD | PHOSPHORUS ESR 1 PTD MN | PHOSPHORUS ESR 1 PTD SD | PHOSPHORUS ESR 4 PTD MN | PHOSPHORUS ESR 4 PTD SD |
|---|---|---|---|---|---|---|---|---|---|---|---|---|
| 4. ethoxylated anhydrosorbitol esters | | Span 60 | ICI Amer | 7.3 cl | 0 | 3 | 0 | 2 | 2 | 6 | −3 | 2 |
| | | Tween 20 | ICI Amer | 4.8 tr | 17 | 2 | −8 | 9 | 17 | 4 | −13 | 9 |
| | | Tween 60 | ICI Amer | 4.4 s. cl | 15 | 6 | −4 | 1 | 15 | 7 | −6 | 2 |
| | | Tween 80 | ICI Amer | | | | | | | | | |
| 5. ethoxylated fats, oils, & waxes | ethoxylated castor oil | Emulphor EL719 | GAF Co | 6.6 tr | 1 | 12 | −16 | 10 | 4 | 8 | −11 | 6 |
| | polyoxyethylene sorbitol oleate-laurate | Atlox 1045A | ICI Amer | 7.0 v. cl | −1 | 7 | −2 | 6 | 6 | 17 | 1 | 7 |
| 6. glycerol esters of fatty acids | polyoxyethylene sorbitol lanolin | G-1441 | ICI Amer | 7.6 s. cl | 8 | 7 | −12 | 9 | 4 | 12 | −11 | 10 |
| | diethylene glycol distearate | | stock | 6.1 i | 7 | 2 | −8 | 8 | 8 | 3 | −8 | 10 |
| C. Carboxylic Amides | | | | | | | | | | | | |
| 1. diethanolamine condensates | | Condensate PO | Con Chem | | | | | | | | | |
| 2. monoalkanolamine condensates | | | | | | | | | | | | |
| 3. polyoxyethylene fatty acid amides | PEG-6-lauramide | Amidox L-5 | Stepan | 9.5 tr | 0 | 4 | −3 | 8 | −1 | 5 | −2 | 7 |
| D. Polyalkene Oxide Block Copolymers | | | | | | | | | | | | |
| 1. poly(oxyethylene-co-oxypropylene) | | Pluronic F127 | ICI Amer | 5.6 tr, fm | −3 | 11 | −7 | 0 | −6 | 13 | −13 | 3 |
| | | Pluronic F87 | ICI Amer | 6.1 tr, fm | 21 | 1 | −3 | 4 | 21 | 3 | −7 | 2 |
| III. CATIONIC | | | | | | | | | | | | |
| A. Amines | | | | | | | | | | | | |
| 1. oxygen-free amines | | | | | | | | | | | | |
| 2. amine oxides | lauramine oxide | Armonyx LO | Stepan | 7.5 tr, fm | 26 | 3 | −8 | 9 | 24 | 2 | −8 | 7 |
| 3. alkylamine ethoxylates | | Triton RW-75 | Rohm/Haas | 10.8 tr | −6 | 8 | −11 | 6 | −7 | 5 | −16 | 2 |
| 4. ethylenediamine alkoxylates | | Tetronic Polyol-704 | BASF Wyn | 9.0 tr | −11 | 10 | −2 | 3 | −16 | 5 | −9 | 5 |
| 5. amines with amide linkages | | | | | | | | | | | | |
| B. Quarternary Ammonium Salts | coco dimethlammonium salt | Andogen 464 | Aldrich | 3.9 cl, fm | 9 | 7 | −11 | 3 | 13 | 5 | −9 | 2 |
| | quarternary ammonium derivative | G-3634A | ICI Amer | 5.0 tr | 1 | 9 | −8 | 0 | −2 | 9 | −8 | 7 |
| | | G-263 | ICI Amer | 3.9 tr | 0 | 1 | −7 | 3 | −3 | 1 | −11 | 5 |
| IV. AMPHOTERIC | | | | | | | | | | | | |
| A. Amino Acids | glycine | | | 6.2 tr | 3 | 6 | 0 | 14 | 5 | 7 | −3 | 17 |
| | cysteine | | | 4.4 tr | 6 | 13 | 6 | 9 | 7 | 12 | 7 | 6 |
| | arginine | | | 11.0 tr | −6 | 10 | −17 | 24 | 8 | 9 | −2 | 19 |
| | aspartic | | | 2.9 tr | −16 | 5 | −15 | 12 | −8 | 5 | −13 | 15 |
| | phenylalanine | | | 5.6 tr | 14 | 12 | 0 | 19 | 13 | 8 | 0 | 18 |
| B. Imidazolinium Derivatives | alkyl betaine | Emcol CC37-18 | Witco | | | | | | | | | |

Abbreviations: tr = transparent or clear, cl = cloudy, i = insoluble, fm = foamy, ppt = precipitate, v = very, s = slightly Table 8 presents the data for the surfactant samples tested without aluminum present. The table lists the chemical class name of the surfactant, the example tested, its corresponding trade name and manufacturer, if appropriate, the pH and visible appearance of a 1% test concentration, and the resulting enamel solubility reduction (ESR) scores. ESR scores represent the percent degree to which the surfactant treatment was able to reduce the dissolution of tooth enamel in acid, both immediately after treatment (1 PTD scores) and following four additional acid demineralizations (4 PTD scores). The higher the score, the better the efficiency of the treatment solution.

In addition to calculating the ESR scores from the amount of enamel calcium found in the demineralization solutions, enamel phosphorous was also measured as a check. Although essentially equivalent, both the calcium and phosphorous ESR scores are presented. Three replicates were conducted in order to establish the mean (MN) and standard deviation (SD) values. Comparing the ESR data in Table 8 to the distilled water control, it is apparent that none of the surfactants by themselves had any significant effect in reducing the acid solubility of enamel. The slight effect noted for Hamposyl L, Igepal CO-660, Pluronic F87, and Ammonyx LO was probably due to a slight coating of the tooth surface by the surfactant. Indeed the 4 PTD scores show that this effect was totally transient with no residual benefit. Most of the surfactant resulted in transparent (tr) aqueous solutions, although some produced cloudy (cl) and even insoluble (i) mixtures.

The corresponding pH, visual compatibility, and ESR data for the same surfactants combined with 0.005 M $AlK(SO_4)_2 \cdot 12H_2O$ are presented in Table 9. A low concentration of 0.005 M aluminum was used so that any minor interference caused by the surfactants would be more readily detected by the ESR procedure. From the data, it is apparent that, compared to the aluminum positive control, the anionic surfactant types generally are not compatible with aluminum and significantly diminish its ability to reduce the acid dissolution of enamel. This is not totally unexpected since the negative charge of such anionic surfactants can combine with the positively charged aluminum cations to inactivate them. Interestingly, the Sandopan MS-40 anionic surfactant is an exception. Sandopan MS-40, a polyethoxycarboxylate, had excellent ESR scores, and could be used in the present aluminum-containing anticariogenic systems. The anionic Triton X-301, an ethoxylated alkylphenol sulfate, also gave an acceptable ESR.

The uncharged, nonionic surfactants resulted in ESR scores indicative of good compatibility with aluminum. All of the positively charged cationic amine surfactants, except for Tetronic Polyol 704 were incompatible with aluminum. Apparently polyalkoxylation of the ethylenediamine moiety results in a predominant aluminum compatible nonionic-like character comparable to the character described for the polyalkoxycarboxylates (sandopan MS-40) above.

TABLE 9
ESR, pH, AND VISUAL APPEARANCE OF 0.005M ALUMINUM WITH ANIONIC, NONIONIC, CATIONIC, AND AMPHOTERIC SURFACTANTS

| TYPE OF SURFACTANT | EXAMPLE TESTED | TRADE NAME | SOURCE | .005M ALUM + 1% SURFACTANT pH SOL. | CALCIUM ESR 1 PTD MN | SD | PTD MN | SD | PHOSPHORUS ESR 1 PTD MN | SD | 4 PTD MN | SD |
|---|---|---|---|---|---|---|---|---|---|---|---|---|
| CONTROL | AlK (SO4)2-12H2O | alum | Baker | 4.0 tr | 80 | 3 | 59 | 5 | 81 | 3 | 61 | 6 |
| I. ANIONIC | | | | | | | | | | | | |
| A. Carboxylates | | | | | | | | | | | | |
| 1. regular | sodium stearate | none | stock | 9.4 ppt, v cl | 47 | 11 | 23 | 5 | 50 | 11 | 23 | 4 |
| 2. polyalkoxycarboxylates | | Sandopan MS-40 | Sandoz | 3.9 s cl | 69 | 5 | 31 | 14 | 70 | 3 | 34 | 12 |
| B. N-Acylsarcosinates | Na lauryl sarcosine | Hamposyl L | WR Grace | 2.5 i, ppt | 57 | 12 | 28 | 2 | 57 | 11 | 31 | 3 |
| | Na lauryl sarcosinate | Hamposyl L-30 | WR Grace | 3.4 ppt, cl | 43 | 4 | 20 | 7 | 46 | 4 | 21 | 9 |
| C. Acylated Protein Hydrolysates | none | none | | | | | | | | | | |
| D. Sulfonates | | | | | | | | | | | | |
| 1. alkylbenzenesulfonates | | Conco AAS-45S | Con Chem | | | | | | | | | |
| 2. alkylarenesulfonates | | | | | | | | | | | | |
| 3. lignosulfonates | | | | | | | | | | | | |
| 4. naphthalenesulfonates | | Daxad 11 | WR Grace | 4.2 ppt, cl | 56 | 2 | 37 | 8 | 56 | 1 | 36 | 8 |
| 5. a-olefinsulfonates | | Conco AOS-40 | Con Chem | | | | | | | | | |
| 6. petroleum sulfonates | | | | | | | | | | | | |
| 7. dialkylsulfosuccinates | | Aerosol OT | Am Cyn | 4.1 ppt, cl | 27 | 7 | −12 | 16 | 27 | 2 | −9 | 13 |
| 8. amidosulfonates | | Concogel | Con Chem | | | | | | | | | |
| 9. acyl isethionates | | Dowfax 2A1 | Dow Chem | 4.1 ppt, s cl | 69 | 4 | 31 | 10 | 66 | 11 | 28 | 9 |
| E. Sulfates and Sulfonated Products | | | | | | | | | | | | |
| 1. alcohol sulfates | Na lauryl sulfate | | stock | 4.2 ppt, fm | 56 | 4 | 27 | 10 | 56 | 2 | 29 | 12 |
| 2. ethoxylated alcohol sulfates | | Conco Sulfate-219 | Con Chem | | | | | | | | | |
| 3. ethoxylated alkylphenol sulfates | | Triton X-301 | Rohm/Haas | 3.9 ppt, s cl | 73 | 9 | 42 | 4 | 68 | 10 | 40 | 4 |
| 4. sulfated acids, amides, & esters | | | | | | | | | | | | |
| 5. sulfated oils & fats | | | | | | | | | | | | |
| F. Phosphate Esters | Na nonoxynol-6 phosphate | Emphos CS-1361 | Witco | | | | | | | | | |
| II. NONIONIC | | | | | | | | | | | | |
| A. Ethoxylates | | | | | | | | | | | | |
| 1. alcohol ethoxylates | alkylated polyether alcohol | Brij 35 | ICI Amer | 3.8 tr | 81 | 2 | 61 | 6 | 82 | 2 | 64 | 4 |
| | | Triton X-100 | Rohm/Haas | 3.7 tr, s ppt | 76 | 10 | 66 | 15 | 79 | 9 | 65 | 14 |
| 2. alkylphenol ethoxylates | | Igepal CO-660 | GAF Co | 4.0 tr | 78 | 4 | 65 | 7 | 80 | 4 | 61 | 7 |
| B. Carboxylic (Fatty) Acid Esters | | | | | | | | | | | | |
| 1. glycerol esters | glycerol monostearate | Adacel 165 | ICI Amer | | | | | | | | | |
| | glycerol & polyoxyethylene stearate | Arlacel 165 | ICI Amer | 3.9 v cl | 80 | 8 | 48 | 10 | 79 | 6 | 46 | 7 |
| 2. polyoxyethylene esters | | Myrj 525 | ICI Amer | 3.8 tr | 74 | 3 | 39 | 8 | 75 | 3 | 39 | 8 |
| | polyoxyethylene 20 isohexadecyl ether | Arlasolve 200 | ICI Amer | 3.9 tr | 80 | 6 | 58 | 5 | 81 | 5 | 57 | 5 |
| 3. anhydrosorbitol esters | | Span 20 | ICI Amer | 3.9 cl | 75 | 6 | 44 | 6 | 79 | 5 | 47 | 9 |
| | | Span 40 | ICI Amer | | | | | | | | | |

TABLE 9-continued

ESR, pH, AND VISUAL APPEARANCE OF 0.005M ALUMINUM
WITH ANIONIC, NONIONIC, CATIONIC, AND AMPHOTERIC SURFACTANTS

| TYPE OF SURFACTANT | EXAMPLE TESTED | TRADE NAME | SOURCE | .005M ALUM + 1% SURFACTANT pH SOL. | CALCIUM ESR 1 PTD MN | CALCIUM ESR 1 PTD SD | CALCIUM ESR PTD MN | CALCIUM ESR PTD SD | PHOSPHORUS ESR 1 PTD MN | PHOSPHORUS ESR 1 PTD SD | PHOSPHORUS ESR 4 PTD MN | PHOSPHORUS ESR 4 PTD SD |
|---|---|---|---|---|---|---|---|---|---|---|---|---|
| 4. ethoxylated anhydrosorbitol esters | | Span 60 | ICI Amer | 4.1 cl | 72 | 9 | 37 | 6 | 73 | 7 | 40 | 7 |
| | | Tween 20 | ICI Amer | 3.8 tr | 73 | 2 | 50 | 9 | 77 | 1 | 50 | 10 |
| | | Tween 60 | ICI Amer | 3.8 cl | 78 | 3 | 66 | 7 | 81 | 3 | 65 | 8 |
| | | Tween 80 | ICI Amer | | | | | | | | | |
| 5. ethoxylated fats, oils, & waxes | ethoxylated castor oil | Emulphor EL719 | GAF Co | 3.9 s cl | 73 | 4 | 35 | 2 | 75 | 4 | 35 | 1 |
| | polyoxyethylene sorbitol oleate-laurate | Atlox 1045A | ICI Amer | 4.0 v cl | 79 | 2 | 44 | 4 | 82 | 2 | 49 | 2 |
| | polyoxyethylene sorbitol lanolin | G-1441 | ICI Amer | 4.0 s cl | 81 | 5 | 47 | 13 | 81 | 6 | 43 | 11 |
| 6. glycerol esters of fatty acids | diethylene glycol distearate | | stock | 3.5 i | 74 | 7 | 39 | 5 | 75 | 6 | 40 | 7 |
| C. Carboxylic Amides | | | | | | | | | | | | |
| 1. diethanolamine condensates | | Condensate PO | Con Chem | | | | | | | | | |
| 2. monoalkanolamine condensates | | | | | | | | | | | | |
| 3. polyoxyethylene fatty acid amides | PEG-6-lauramide | Amidox L-5 | Stepan | 4.2 cl | 67 | 16 | 38 | 4 | 67 | 15 | 39 | 3 |
| D. Polyalkene Oxide Block Copolymers | | | | | | | | | | | | |
| 1. poly(oxyethylene-co-oxypropylene) | | Pluronic F127 | ICI Amer | 3.8 tr, fm | 77 | 5 | 52 | 17 | 76 | 4 | 49 | 11 |
| | | Pluronic F87 | ICI Amer | 3.8 tr, fm | 81 | 2 | 67 | 2 | 79 | 2 | 61 | 5 |
| III. CATIONIC | | | | | | | | | | | | |
| A. Amines | | | | | | | | | | | | |
| 1. oxygen-free amines | | | | | | | | | | | | |
| 2. amine oxides | lauramine oxide | Armonyx LO | Stepan | 4.3 ppt, cl | 36 | 9 | 21 | 8 | 38 | 10 | 24 | 6 |
| 3. alkylamine ethoxylates | | Triton RW-75 | Rohm/Haas | 8.8 s cl | 1 | 9 | −20 | 8 | 4 | 8 | −23 | 11 |
| 4. ethylenediamine alkoxylates | | Tetronic Polyol-704 | BASF Wyn | 4.0 s cl | 82 | 6 | 53 | 8 | 81 | 4 | 47 | 5 |
| 5. amines with amide linkages | | | | | | | | | | | | |
| B. Quarternary Ammonium Salts | coco dimethlammonium salt | Andogen 464 | Aldrich | 3.5 cl, fm | 80 | 8 | 52 | 17 | 77 | 8 | 51 | 17 |
| | quarternary ammonium derivative | G-3634A | ICI Amer | 4.0 tr | 77 | 3 | 38 | 6 | 75 | 2 | 36 | 5 |
| | | G-263 | ICI Amer | 3.9 tr | 81 | 3 | 61 | 2 | 83 | 2 | 61 | 2 |
| IV. AMPHOTERIC | | | | | | | | | | | | |
| A. Amino Acids | glycine | | | 4.0 cl | 50 | 3 | 30 | 7 | 54 | 3 | 34 | 9 |
| | cysteine | | | 2.9 tr | 71 | 2 | 40 | 9 | 74 | 1 | 42 | 10 |
| | arginine | | | 9.8 cl | 7 | 10 | −24 | 22 | 17 | 11 | −16 | 24 |
| | aspartic | | | 2.9 tr | 40 | 8 | 18 | 7 | 37 | 9 | 18 | 6 |
| | phenylalanine | | | 3.7 s cl | 70 | 9 | 48 | 9 | 68 | 7 | 38 | 8 |
| B. Imidazolinium Derivatives | alkyl betaine | Emcol CC37-18 | Witco | | | | | | | | | |

Abbreviations: tr = transparent or clear, cl = cloudy, i = insoluble, fm = foamy, ppt = precipitate, v = very, s = slightly The incompatibility of amines with aluminum in aqueous solution is due to the relatively high pH of the amines and/or formation of an insoluble aluminum amide salt. The cationic quaternary ammonium salts are, however, functional with aluminum. Regarding the dual charged amphoteric surfactants, those derived from amino acids of glycine, cysteine, and phenylalanine resulted in acceptable ESR scores. Surfactants derived from arginine and aspartic acid provided low ESR scores, presumably because of their inherent high and low pH, respectively.

Based on the results of surfactant/aluminum compatibility tests, compatible surfactant blends can also be utilized to obtain the optimum HLB (hydrophilic-lipophilic balance) required to meet the needs of any particular aluminum emulsion system.

We claim:

1. A palatable anticariogenic composition adapted for application to teeth, said composition having a pH of about 2.5 to about 5.0 and comprising
   about 10 to about 50,000 ppm aluminum ions capable of reacting with the teeth,
   water, and
   a surfactant selected from the group consisting of polyalkoxylated anionic surfactants, cationic polyalkoxyamines, quaternary ammonium salts, and amphoteric surfactants derived from amino acids selected from the group consisting of glycine, cysteine, and phenylalanine, said surfactants being present in an amount effective to stabilize the anticariogenic composition.

2. The anticariogenic composition of claim 1 in the form of a product selected from the group consisting of a dental rinse, a mouthwash, a toothpaste, a prophylaxis paste, a chewing gum, and a lozenge.

3. The composition of claim 1 further comprising an ingredient selected from the group consisting of about 1 to about 90 weight percent of a humectant selected from glycerin and sugar alcohols, a sweetener, and from about 0.1 to about 5.0 weight percent of a flavor oil, and wherein the aluminum ions are present at a level of about 250 to about 2000 ppm.

4. The composition of claim 3 wherein the humectant is selected from the group consisting of glycerin, xylitol, mannitol and sorbitol.

5. The composition of claim 3 wherein in the sweetener comprises a non-cariogenic sweetener selected from the group consisting of saccharin, cyclamate and aspartame.

6. The composition of claim 1 wherein the surfactant has an HLB of between about 9 and about 30.

7. The composition of claim 6 wherein the surfactant is selected from the group consisting of polyalkoxylated anionic surfactants and cationic polyalkoxyamines.

8. The composition of claim 6 wherein the surfactant is a quaternary ammonium salt.

9. The composition of claim 6 wherein the surfactant is a derivative of an amino acid selected from the group consisting of glycine, cysteine and phenylalanine.

10. A palatable anticariogenic emulsion adapted for application to teeth, said composition have a pH of about 2.5 to about 5.0 and comprising
    about 10 to about 50,000 ppm aluminum ions capable of reacting with teeth,
    water,
    a surfactant selected from the group consisting of non-ionic surfactants, polyalkoxylated anionic surfactants, cationic polyalkoxyamines, quarternary ammonium salts, and amphoteric surfactants derived from amino acids selected from the group consisting of glycine, cysteine, and phenylalanine,
    about 1 to about 90 weight percent of a humectant selected from glycerine and sugar alcohols,
    a sweetener, and
    from about 0.1 to about 5.0 weight percent of a flavor oil, said surfactant being present in an amount effective to stabilize the anticariogenic emulsion.

11. The emulsion of claim 10 wherein the aluminum ions are present at a level of about 250 to about 2,000 ppm.

* * * * *